United States Patent
Govari et al.

(10) Patent No.: US 11,622,698 B2
(45) Date of Patent: Apr. 11, 2023

(54) SELECTING CURSOR LOCATIONS ON MEDICAL IMAGE USING DIRECTIONS FROM DISTAL END OF PROBE

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 569 days.

(21) Appl. No.: 16/720,135

(22) Filed: Dec. 19, 2019

(65) Prior Publication Data
US 2021/0186362 A1 Jun. 24, 2021

(51) Int. Cl.
A61B 5/06 (2006.01)
A61B 34/20 (2016.01)
A61B 34/00 (2016.01)

(52) U.S. Cl.
CPC .............. *A61B 5/062* (2013.01); *A61B 34/20* (2016.02); *A61B 34/70* (2016.02); *A61B 2034/2051* (2016.02); *A61B 2034/731* (2016.02)

(58) Field of Classification Search
CPC .............. A61B 17/24; A61B 2034/107; A61B 2034/2051; A61B 2034/2072; A61B 2034/731; A61B 34/20; A61B 34/25; A61B 34/70; A61B 5/062
See application file for complete search history.

(56) References Cited

U.S. PATENT DOCUMENTS

| | | |
|---|---|---|
| 7,996,064 B2 | 8/2011 | Simon et al. |
| 2005/0182295 A1 | 8/2005 | Soper et al. |
| 2007/0208252 A1 | 9/2007 | Makower |
| 2016/0183841 A1 | 6/2016 | Duindam et al. |
| 2018/0228392 A1 | 8/2018 | Govari et al. |
| 2019/0090959 A1 | 3/2019 | Haider et al. |
| 2019/0175062 A1 | 6/2019 | Rafii-Tari et al. |
| 2019/0374280 A1 | 12/2019 | Salazar et al. |

FOREIGN PATENT DOCUMENTS

EP  1743575  1/2007

OTHER PUBLICATIONS

International Search Report dated Mar. 5, 2021 from corresponding PCT Patent Application No. PCT/IB2020/060835.

*Primary Examiner* — Michael T Rozanski
(74) *Attorney, Agent, or Firm* — Frost Brown Todd LLP

(57) ABSTRACT

A medical probe includes a tubular distal end section, which is configured to be inserted into a cavity of a patient, and includes (a) a visually guiding object disposed over a perimeter of the distal end section, and (b) a magnetic field sensor including two sensor coils aligned non-parallel with each other, the sensor attached to the distal end section, and having: (i) a first axis of symmetry, of one of the coils, which is aligned perpendicular to a central longitudinal axis of the distal end section, and (ii) a second axis of symmetry, of the remaining coil, which is aligned perpendicular to the central longitudinal axis of the distal end section and not parallel to the first axis of symmetry.

15 Claims, 4 Drawing Sheets

SELECTING CURSOR LOCATIONS ON MEDICAL IMAGE USING DIRECTIONS FROM DISTAL END OF PROBE

FIELD OF THE INVENTION

The present invention relates generally to medical probes, and particularly to ear-nose-throat (ENT) tools.

BACKGROUND OF THE INVENTION

Techniques to guide an invasive probe inside a cavity of an organ to target tissue have been previously proposed in the patent literature. For example, U.S. Patent Application Publication 2019/0090959, published on Mar. 28, 2019, issued as U.S. Pat. No. 11,464,574 on Oct. 11, 2022, describes a number of improvements related to computer aided surgery (CAS) utilizing an on-board tool tracking (OTT) system. Some of the improvements relate to methods of providing feedback during a procedure to improve either the efficiency or quality, or both, for a procedure including the rate of and type of data processed depending upon a CAS mode. In an embodiment, to provide navigation assistance during an OTT CAS procedure, an OTT device monitors the position of the associated surgical tool within the surgical field. The OTT CAS system may use none, or one or more reference frames, including one or more position sensors or one or more fiducial markers depending upon the requirements of the OTT CAS procedure being undertaken.

As another example, U.S. Patent Application Publication 2016/0183841, published on Jun. 30, 2016, describes a method of guiding an interventional instrument within a patient anatomy that comprises processing a target location within the patient anatomy and receiving a position for a tip portion of an interventional instrument at a first location within the patient anatomy. The method also comprises determining a three-dimensional distance between the first location and the target location and displaying a symbol representing the target location and a symbol representing the tip portion of the interventional instrument. In an embodiment, a rotational orientation of a feature of the distal tip portion may also be displayed by the navigation aid image with a rotation assistance symbol. For example, if a biopsy instrument has a side opening, the side with the opening may be indicated on the navigation aid image with the rotation assistance symbol.

U.S. Patent Application Publication 2007/0208252, published on Sep. 6, 2007, now abandoned, describes devices, systems and methods for performing image guided interventional and surgical procedures, including various procedures to treat sinusitis and other disorders of the paranasal sinuses, ears, nose or throat. In some applications, a preoperative tomographic scan (e.g., a CT scan) may be obtained and the image guidance system may be programmed to display the tomographic images on a video monitor along with a real time indication (e.g., cross hairs, an illuminated dot, etc.) of the location of the working device relative to the anatomical structures shown on the tomographic image.

SUMMARY OF THE INVENTION

An embodiment of the present invention includes a medical probe including a tubular distal end section, which is configured to be inserted into a cavity of a patient, and includes (a) a visually guiding object disposed over a perimeter of the distal end section, and (b) a magnetic field sensor including two sensor coils aligned non-parallel with each other, the sensor attached to the distal end section, and having: (i) a first axis of symmetry, of one of the coils, which is aligned perpendicular to a central longitudinal axis of the distal end section, and (ii) a second axis of symmetry, of the remaining coil, which is aligned perpendicular to the central longitudinal axis of the distal end section and not parallel to the first axis of symmetry.

In some embodiments, the visually guiding object includes a guiding bump. In other embodiments, the visually guiding object includes one or more colored angular sections of the perimeter of the distal end section.

In an embodiment, the two sensor coils are mutually orthogonal.

There is additionally provided, in accordance with another embodiment of the present invention, a system including a probe and a processor of magnetic tracking system. The probe includes a tubular distal end section, which is configured to be inserted into a cavity of a patient, and includes (a) a visually guiding object disposed over a perimeter of the distal end section, and (b) a magnetic field sensor including two sensor coils aligned non-parallel with each other, the sensor attached to the distal end section, and having: (i) a first axis of symmetry, of one of the coils, which is aligned perpendicular to a central longitudinal axis of the distal end section, and (ii) a second axis of symmetry, of the remaining coil, which is aligned perpendicular to the central longitudinal axis of the distal end section and not parallel to the first axis of symmetry. The processor of the magnetic tracking system is configured to: (a) using signals received from the magnetic field sensor coils, calculate a position, direction and rotational orientation of the distal end in the cavity of the patient, (b) register the measured position with a medical image, (c) using the calculated direction and rotational orientation, find in the medical image a first location along the direction of the central longitudinal axis, and a second location along a direction from the calculated position to the object, and (d) toggle a cursor between the first and second locations on the medical image.

In some embodiments, the system further includes colored angular sections over the perimeter of the distal edge of the distal end section, wherein based on the known orientations of the colored angular sections relative to the second axis of symmetry, the processor is further configured to define the object as any of the colored angular sections, which is viewed using an endoscope inserted into the cavity, and toggle a cursor between the first and second locations on the medical image accordingly.

There is further provided, in accordance with another embodiment of the present invention, a method for toggling a cursor on a medical image of an organ of patient, the method includes inserting a tubular distal end section of a probe into a cavity of an organ of a patient, wherein the distal end includes (a) a visually guiding object disposed over a perimeter of the distal end section, and (b) a magnetic field sensor including two sensor coils aligned non-parallel with each other, the sensor attached to the distal end section, and having: (i) a first axis of symmetry, of one of the coils, which is aligned perpendicular to a central longitudinal axis of the distal end section, and (ii) a second axis of symmetry, of the remaining coil, which is aligned perpendicular to the central longitudinal axis of the distal end section and not parallel to the first axis of symmetry. Using signals received from the magnetic field sensor coils, a position, direction and rotational orientation of the distal end in the cavity of the patient are calculated. The measured position is registered with a medical image. Using the calculated direction and rotational orientation, founded in the medical image are a first location along the direction of the central longitudinal axis and a second location along a direction from the calculated position to the object. A cursor is toggled between the first and second locations on the medical image.

In some embodiments, the method further includes defining the object as a colored angular section among colored angular sections over a perimeter of a distal edge of the distal end section, which is viewed using an endoscope inserted into the cavity. Based on the known orientations of the colored angular sections relative to the second axis of symmetry, a cursor is toggled between the first and second locations on the medical image accordingly.

The present invention will be more fully understood from the following detailed description of the embodiments thereof, taken together with the drawings in which:

DETAILED DESCRIPTION OF EMBODIMENTS

Overview

Figure 1:
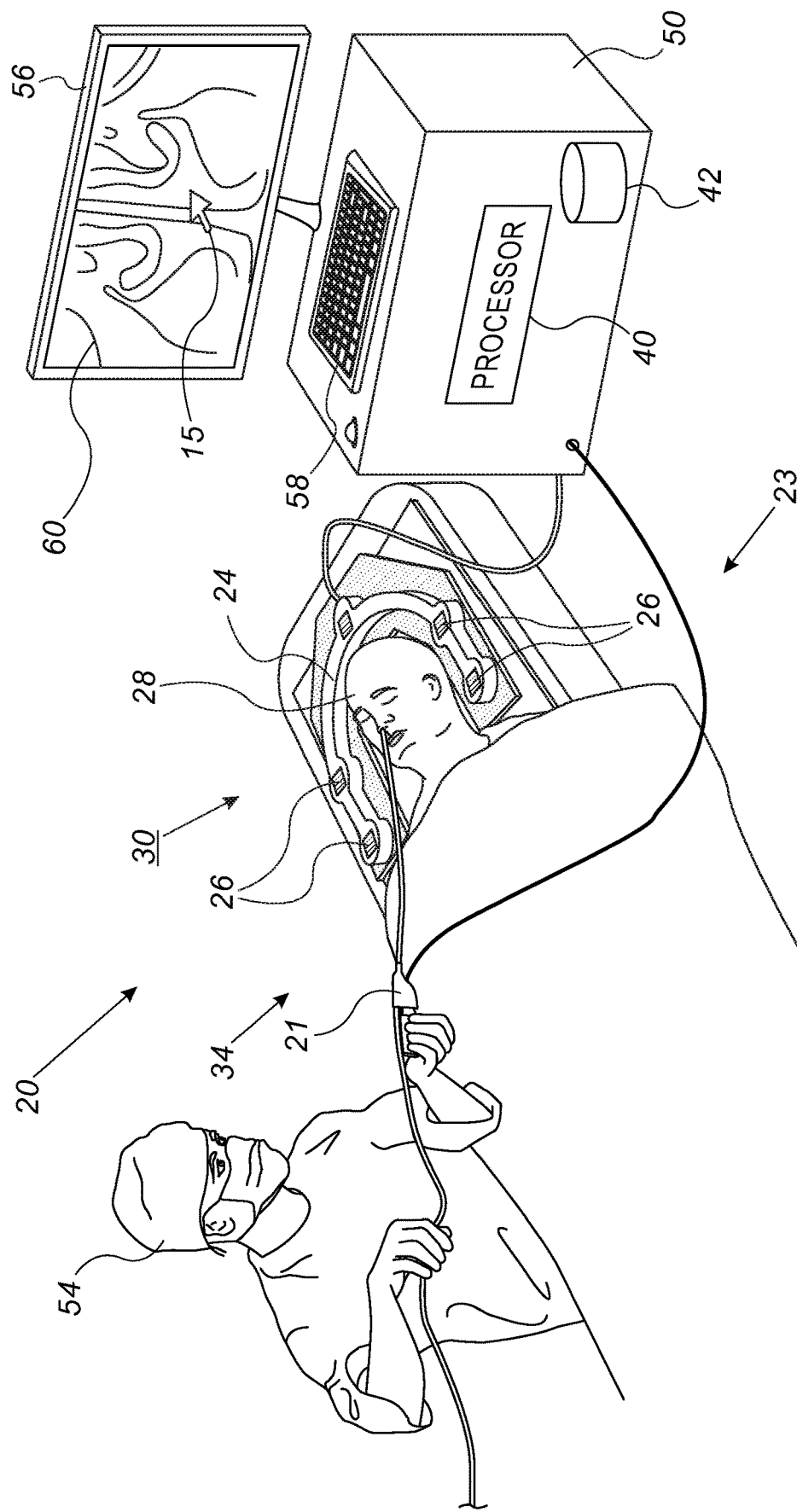
FIG. 1 is a schematic, pictorial illustration of an ear-nose-throat (ENT) system, in accordance with an embodiment of the present invention.

A distal end section of a probe, such as an ear-nose-throat (ENT) probe used with a guiding system, can be tracked to be visually used as a cursor (i.e., pointer) of a location in a 3D view (e.g., medical image) of a cavity of a patient. For example, an ENT suction tool, or a shaver, can be used in such a way with the TruDi™ ENT tracking system (made by Acclarent, Irvine, Calif.). The medical image can be generated, for example, from a CT or MRI image.

The distal end section of the probe (e.g., an ENT suction device) can be tracked using a magnetic sensor attached to the distal end, with the tracked position projected onto a location on the medical image along a direction of a center longitudinal axis of the distal end (e.g., center of a suction aperture of the suction tool). In this manner, a physician can view a cursor location on the medical image (on a display) as if "viewed" distally from the tool itself.

However, for some clinical procedures, it might be preferable for the user to toggle the image cursor between an image location projected along the center longitudinal direction, and a different image location corresponding to a visually-guiding object disposed on a perimeter of the distal edge of the distal end of the probe. The different image locations are interchangeably viewed as if viewed distally from the tool via virtual crosshairs put, for example, by the physician using a user interface of the position tracking system, on center and perimeter tracked positions on the distal edge of the distal end of the probe.

Embodiments of the present invention that are described hereinafter provide means that allow a user to toggle the displayed cursor on a 3D view (e.g., a medical image) between medical image locations received by projecting the tracked position along the above two different directions. In one embodiment, the tracked object is a guiding bump, as described below. In another embodiment, the distal edge of the tubular distal end section (e.g., nosepiece) is colored to show several angular sections (e.g., four quadrants) that each of can be tracked based on user decision on which of the sections to put the crosshair.

Using a video image from an endoscope (e.g., otoscope) inserted into the cavity, the physician can see the bump or at least part of the angular sections in real time, as well see target tissue (e.g., polyp) and nearby tissue not to affect with the tool (e.g., brain tissue). Based on known orientations of the colored angular sections relative to the object, a processor redefines the object as any of the colored angular sections viewed using the endoscope, and toggles a cursor on the medical image accordingly.

Typically, at a beginning of a medical procedure, frames of reference of the medical image and the magnetic tracking system are registered. The position, direction and angular orientation of the sensor are tracked by the system to enable putting crosshairs at the different tracked positions to thereby enable toggling the cursor on the medical image between the central and tilted directions, as described above.

The disclosed techniques allow a physician to direct the distal edge of the ENT tool to a target an intrabody location with the distal edge of the tool optimally aligned in position, direction, and rotational orientation for performing, for example, a therapeutic procedure, such as ENT suction.

System Description

FIG. 1 is a schematic, pictorial illustration of an ear-nose-throat (ENT) system 20, in accordance with an embodiment of the present invention. In the following description an ENT tool 21 in system 20 is assumed to be used to perform a suction procedure in the sinuses of a patient 28, although it will be understood that the tool may be used to perform other procedures on the patient.

As is described below, in an embodiment, tool 21 comprises a tilted dual axis magnetic sensor 34 attached to a distal end (distal end and sensor described in FIG. 2) of tool 21, which is tracked during the procedure by a magnetic tracking system 23. For the tracking to be effective in system 20, frames of reference of a medical image 60, e.g., computerized tomography (CT) images of patient 28, and of magnetic tracking system 23, are registered. While CT image 60 may typically comprise a magnetic resonance imaging (MRI) image or a fluoroscopic image, in the description herein the image is assumed to comprise, by way of example, a fluoroscopic CT image.

Prior to and during the sinus procedure, a magnetic radiator assembly 24, comprised in the magnetic tracking system, is positioned beneath the patient's head. Assembly 24 comprises magnetic field radiators 26 which are fixed in position and which transmit alternating magnetic fields into a region 30 wherein the head of patient 28 is located. Potentials generated by sensor 34 in region 30, in response to the magnetic fields, enable the measurement of its position, direction, and angular orientation in the magnetic tracking system's frame of reference.

By way of example, five radiators 26 of assembly 24 are arranged in an approximately horseshoe shape around the head of patient 28. However, alternate configurations for the radiators of assembly 24 may be used, and all such configurations are assumed to be comprised within the scope of the present invention.

Prior to the procedure, the registration of the frames of reference of the magnetic tracking system with the CT image may be performed by positioning a magnetic sensor at known positions of the image, such as the end of the patient's nose. However, any other convenient system for registration of the frames of reference may be used.

Elements of system 20 are under overall control of a system processor 40. Processor 40 may be mounted in a console 50, which comprises operating controls 58 that typically include a keypad and/or a pointing device such as a mouse or trackball. Console 50 connects to radiators 26 and to sensor 34 wirelessly and/or via one or more cables. A physician 54 uses operating controls 58 to interact with the processor while performing the ENT procedure using system 20. While performing the procedure, the processor presents a cursor 15 on medical image 60 on a screen 56 to assist the physician in guiding the distal end to a target tissue location in the sinuses.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Figure 2:
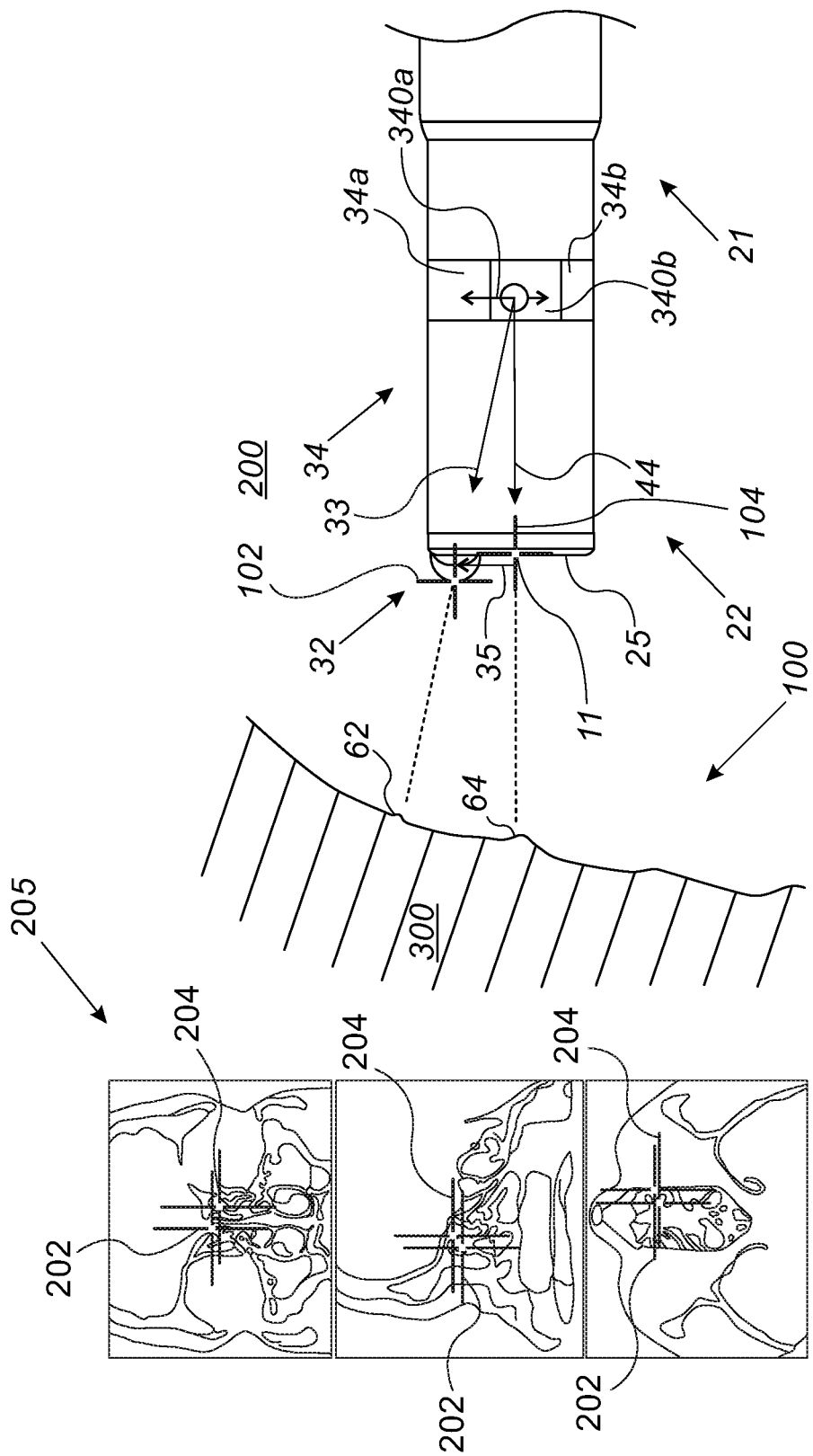
FIG. 2 is a side view of the distal end of the ear-nose-throat (ENT) tool used in FIG. 1, in accordance with an embodiment of the present invention.

Toggling Cursor Between Locations on Medical Image According to Directions of Bump and Center Directions FIG. 2 is a side view of a distal end section 22 of the ear-nose-throat (ENT) tool 21 used in FIG. 1, in accordance with an embodiment of the present invention. Distal end section 22 comprises a dual axis coil sensor 34, which its two coils (34a, 34b) are aligned non-parallel with each other. Both coils 34a and 34b have their axes of symmetry (340a, 340b) aligned perpendicularly to a direction 44 of a central axis of the distal end. For any given direction of the distal end relative to the direction of the magnetic field of system 20, and for any roll angle about axis 44, dual-axis sensor 34 allows system 20 to find tilted direction 33 and center longitudinal direction 44 and use the direction as described below.

On insertion of tool 21, distal end section 22 of the tool is typically in air, i.e., is in a cavity region 200 of a schematically illustrated anatomy 100, that corresponds to a zero Hounsfield Unit (HU) value in 3 planes of a medical image, such as a CT image 205 of the anatomy. During the medical procedure, the nosepiece is conveniently observed with an endoscope (not shown), which is typically operated by the physician to acquire and display a video image, so that the physician can see the location of the nosepiece relative to anatomy 100. As seen in FIG. 2, anatomy 100 comprises anatomical features at surface locations 62 and 64 that the physician wants to view with the endoscope.

In the shown embodiment, the processor projects the position of sensor 34 onto the anatomy in directions defined by tracked center position 11 and bump 32 position over the perimeter of the distal edge of distal end section 22. In the shown embodiment, positions 11 and 32 define directions 33 and 44, respectively. The frames of reference of CT 205 image and the magnetic tracking system are registered, so that processor 40 can use an actually aimed at anatomical location by distal end 22 to mark a matching location on image 205 with a cursor. Thus, the tracking system relates the visually viewed locations 62 and 64 that a physician aiming the ENT tool at these wishes to resolve, to respective locations 202 and 204 in 3 planes of CT image 205.

To select direction 33 or 44 of the tool relative to anatomy, the physician puts, using a user interface, virtual crosshairs 102 and 104 on positions, such as positions 11 and 32, respectively. The physician may move a crosshair to any other arbitrary tilted location over the distal perimeter, which results in the cursor marking another location than location 62 on CT image 205. Therefore, the physician may toggle the cursor on the medical image between a first location 302 and a second location 304, that match preselected crosshairs locations 102 or 104 on the tool, so as to view anatomy locations 62 or 64 from direction 33 and 44, respectively.

Toggling the cursor on the planes of CT image 205 between locations 302 and 304 therein, in correspondence to actual anatomical locations 62 and 64 pointed at by different portions of distal end section 22, respectively, allows the physician better control on the use of the tool on either marked tissue locations.

Note, only a single cursor is presented at all times on a plane of CT image 205, and showing the cursor for both locations 302 and 304 in FIG. 2 is done purely for the purpose of describing the toggling of the cursor according to chosen positions on the medical tool to put at (by software) crosshairs 102 and 104.

The magnetic navigation system can further tell the physician how far the nearest tissue location is (e.g., locations 62 or 64) from bump 32 or center location 11. The processor may display a distance from the selected tracked location on the tool to the nearest tissue region (an area having non-zero HU values) in order to aid the physician in assessing proximity.

Figure 3:
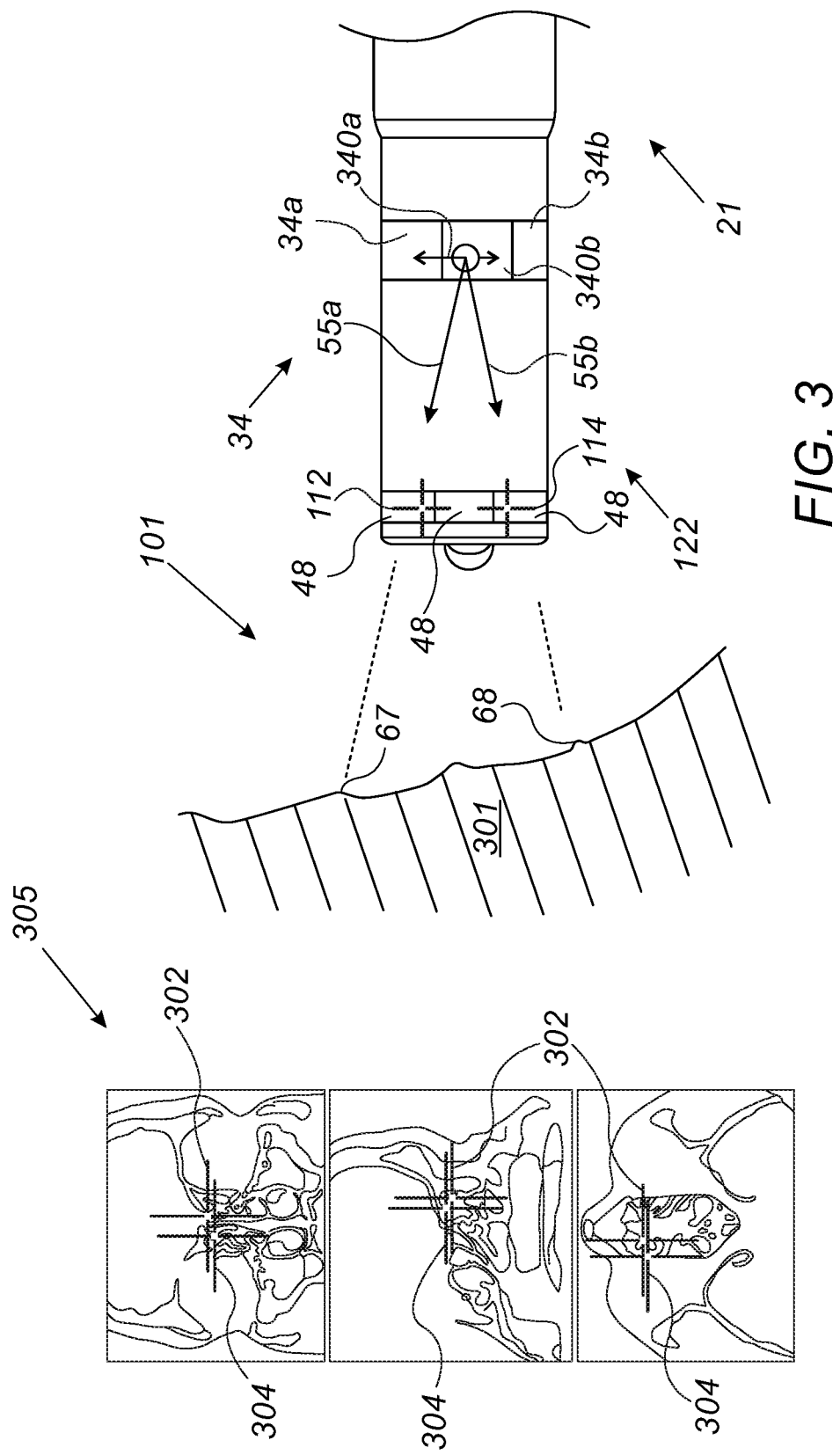
FIG. 3 is a top view of a distal end of an ear-nose-throat (ENT) tool, in accordance with another embodiment of the present invention.

Toggling Cursor Between Locations on Medical Image According to Directions of Angular Sections FIG. 3 is a top view of a distal end section 122 of the ear-nose-throat (ENT) tool, in accordance with another embodiment of the present invention. In the shown embodiment, dual-axis magnetic sensor 34 is the same as in FIG. 2.

As seen in FIG. 3, the nosepiece of distal end 122 is visually marked (e.g., colored) into quadrants 48. In the shown embodiment, one of colored quadrants 48 defines a direction 55a while another of colored quadrants 48 defines a direction 55b. Based on the known geometry of the distal end, and using sensor 24, crosshairs can be put on any of the position tracked quadrants 48, where in the shown embodiment, the physician have put crosshairs 112 and 114 on quadrant locations that defines directions 55a and 55b, respectively. As described above, a cursor appearing on a registered medical image, such as 3 plane CT image 305, on can be toggled between corresponding locations 302 and 304, respectively. Note again, only a single cursor is presented at all times on each plane of a medical image.

While observing the nosepiece with the endoscope, the physician can toggle between the different quadrants, and so choose the cursor for the 3D view to be in a location and direction that corresponds to an angular segment the physician selects to have a crosshair on. For example, based on a physician selection, processor 40 can select one of quadrants to have the cursor pointing at a location 302 on the medical image that corresponds to an anatomy location 67 in region 301 of anatomy 101, projected along a direction 55a via crosshairs positioned (102) on that quadrant, or have the cursor pointing at a location 304 on the medical image that corresponds to an anatomy location 68 in region 301 of anatomy 101 having non-zero HU, projected along a direction 55b via crosshairs 104 positioned (104) as seen on another quadrant.

Hardware Implementations of the Probe

Figure 4:
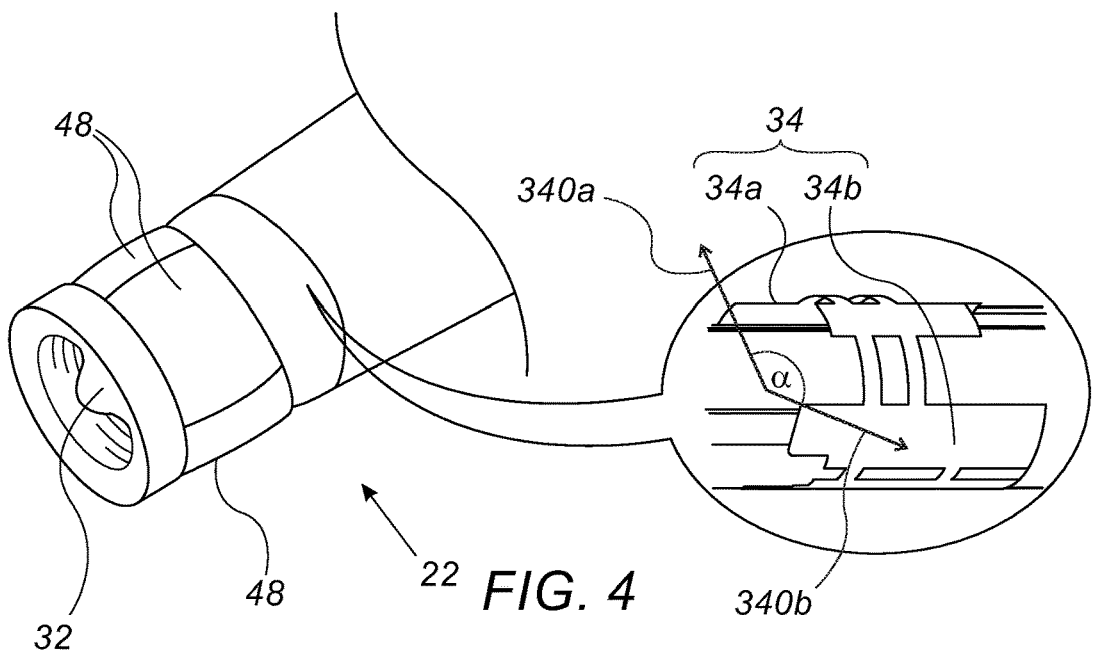
FIG. 4 is a perspective view of a distal end of an ear-nose-throat (ENT) tool that shows implementations of elements of the ENT tools of FIGS. 2 and 3, in accordance with embodiments of the present invention.

FIG. 4 is a perspective view of a distal end section 222 of ear-nose-throat (ENT) tool 211 that shows implementations of elements of the ENT tools of FIGS. 2 and 3, in accordance with embodiments of the present invention. Such a perspective view of distal end section 222 may be part of a video image taken by the aforementioned endoscope.

In the shown embodiment, coils 34a and 34b of a transverse dual axis sensor 134 are formed so that their axes of symmetry 340a and 340b are with an angle α between them. The axes are non-parallel to each other and in typically are closer to be orthogonal (in the shown embodiment α~120 degrees). Dual axis sensor 34 is configured to provide different sets of voltage signals according to the rotational orientation of distal end 22 about axis 44 (seen in FIG. 2).

Forming a multi-axis magnetic sensor on a distal end, such as sensor 134, was described in U.S patent Application Publication 2018/0228392 which describes a position sensor including a flexible substrate formed into a three-dimensional (3D) shape, which is assigned to the assignee of the present patent application. There, at least first and second field-sensing coils are formed in first and second respective layers of the flexible substrate, such that in the 3D shape the first and second field-sensing coils have first and second respective axes that are not parallel to one another.

FIG. 4 also visualizes the aforementioned guiding bump and angular sections 48 (e.g., quadrants 48) that are visually marked (e.g., colored) over distal end 22 (i.e., the nosepiece).

Toggling Cursor Location Procedures

Figure 5:
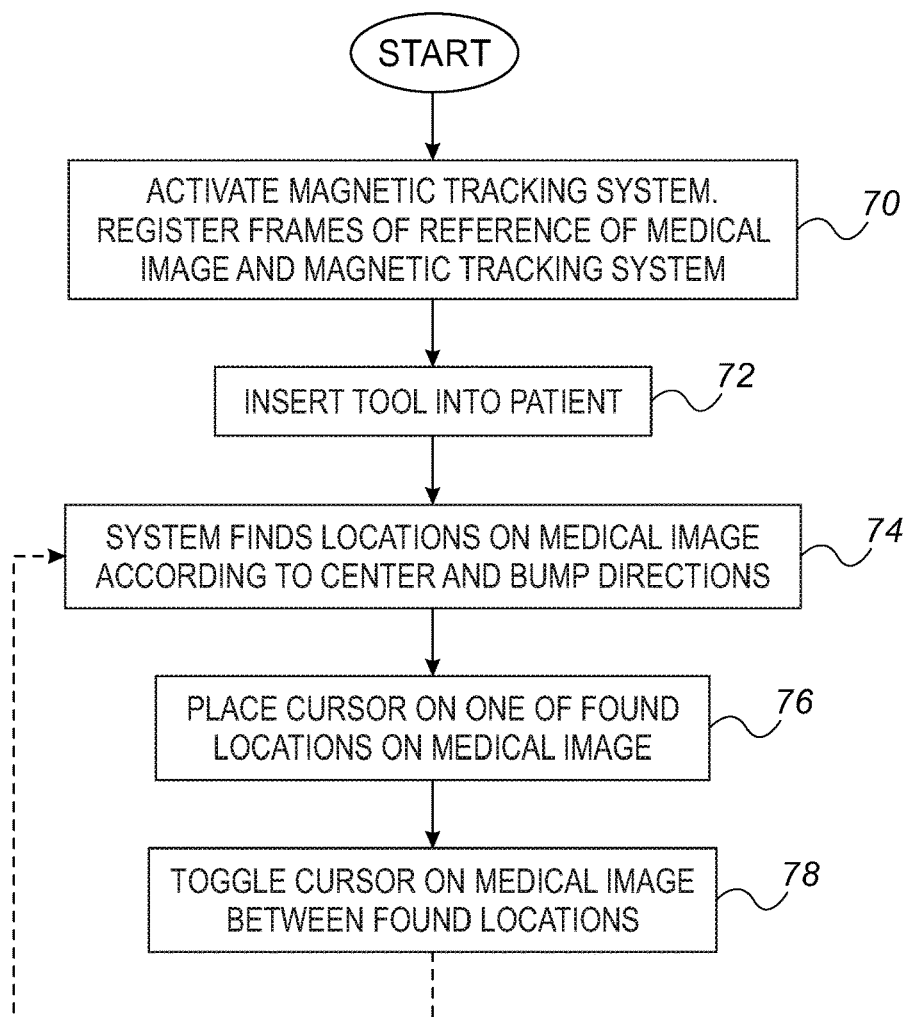
FIG. 5 is a flow chart of a method for toggling a cursor between locations on a medical image using the distal end of the ear-nose-throat (ENT) tool of FIG. 2, in accordance with an embodiment of the present invention.

FIG. 5 is a flow chart of a method for toggling a cursor between locations on a medical image using distal end section 22 of ear-nose-throat (ENT) tool 21 of FIG. 2, in accordance with another embodiment of the present invention. The process begins with an initial step 70, in which the frames of reference of magnetic tracking system 23 and a medical image, such as derived from CT images of patient 28, are registered, as described above. In order to perform registration with the medical image, magnetic tracking system 23 is activated and is used to track the position, direction, and angular orientation of dual axis sensor 34, as described above. The tracking is assumed to be updated in real time.

In an insertion step 72, physician 54 inserts distal end section 22 of tool 21 into a nostril of patient 28. Once inserted, using the signals from sensor 34, processor 40 finds locations on the medical image of nearest internal elements of patient 28 from virtual crosshairs positioned on distal end section 22 of tool 21, in a range finding step 74.

Next, at a cursor placement step 76, processor 40 places a cursor over the medical image, so as to point to the nearest internal element of patient 28 to the specified location of distal end section 22 of tool 21.

At a cursor toggling step 78, physician 54 toggles the cursor on the medical image between two imaged locations that correspond to the crosshairs put at the two tracked locations on the distal end section 22 of tool 21. As the physician moves the distal end the process repeats itself, as indicated by the dashed direction line: the cursor locations on the medical image change while the physician continues to move the device or toggle the cursor.

The example flow chart shown in FIG. 5 was chosen purely for the sake of conceptual clarity. FIG. 5 shows only steps relevant to embodiments of the present invention. Other steps, such as selecting tracked positions other than center 11 and bump 32 on the distal end section 22 of tool 21 to put the crosshairs on and subsequently toggle the cursor between newly selected respective locations on the medical image are omitted.

Although the embodiments described herein mainly address ENT applications, the methods and systems described herein can also be used in other applications, such as in cardiac, neurological, or ophthalmic applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A system, comprising:
   (a) a probe, comprising a tubular distal end section configured to be inserted into a cavity of a patient, wherein the tubular distal end comprises:
      (i) a visually guiding object disposed over a perimeter of a distal edge of the distal end, and
      (ii) a magnetic field sensor comprising two sensor coils aligned non-parallel with each other, the sensor attached to the distal end section, and having:
         (A) a first axis of symmetry, of one of the coils, which is aligned perpendicular to a central longitudinal axis of the distal end section, and
         (B) a second axis of symmetry, of the remaining coil, which is aligned perpendicular to the central longitudinal axis of the distal end section and not parallel to the first axis of symmetry; and
   (b) a processor of a magnetic tracking system, which is configured to:
      (i) using signals received from the magnetic field sensor coils, calculate a position, direction and rotational orientation of the distal end in the cavity of the patient,
      (ii) register the calculated position with a medical image,
      (iii) using the calculated direction and rotational orientation, find in the medical image:
         (A) a first location along the direction of the central longitudinal axis, and
         (B) a second location along a direction that extends along an axis passing through the calculated position and the visually guiding object; and
      (iv) toggle a cursor between the first and second locations on the medical image.

2. The system according to claim 1, wherein the visually guiding object is a guiding bump.

3. The system according to claim 1, and comprising a plurality of colored angular sections over the perimeter of the distal edge of the distal end section, wherein based on a known orientation of the plurality of colored angular sections relative to the second axis of symmetry, the processor is further configured to define the object as any of the colored angular sections, which is viewed using an endoscope inserted into the cavity, and toggle the cursor between the first and second locations on the medical image accordingly.

4. A method for toggling a cursor on a medical image of an organ of patient, the method comprising:
(a) inserting a tubular distal end section of a probe into a cavity of an organ of a patient, wherein the distal end comprises:
   (i) a visually guiding object disposed over a perimeter of a distal edge of the distal end, and
   (ii) a magnetic field sensor comprising two sensor coils aligned non-parallel one with each other, the sensor attached to the distal end section, and having:
      (A) a first axis of symmetry, of one of the coils, which is aligned perpendicular to a central longitudinal axis of the distal end section, and
      (B) a second axis of symmetry, of the remaining coil, which is aligned perpendicular to the central longitudinal axis of the distal end section and not parallel to the first axis of symmetry;
(b) using signals received from the magnetic field sensor coils, calculating a position, direction and rotational orientation of the distal end in the cavity of the patient;
(c) registering the calculated position with a medical image;
(d) using the calculated direction and rotational orientation, finding in the medical image:
   (i) a first location along the direction of the central longitudinal axis, and
   (ii) a second location along a direction that extends from the calculated position through the visually guiding object; and
(e) toggling a cursor between the first and second locations on the medical image.

5. The method according to claim 4, wherein the object is a guiding bump.

6. The method according to claim 4, and comprising defining the object as a colored angular section among colored angular sections over the perimeter of the distal edge of the distal end section, which is viewed using an endoscope inserted into the cavity, and, based on a known orientations of the colored angular sections relative to the second axis of symmetry, toggling the cursor between the first and second locations on the medical image accordingly.

7. The method of claim 4, wherein the tubular distal end section comprises a suction instrument.

8. The method of claim 4, further comprising displaying the medial image on a screen.

9. The method of claim 8, wherein the toggling is performed via a keyboard.

10. The method of claim 4, wherein the cursor comprises a cross-hair display.

11. The method of claim 4, further comprising generating an alternating magnetic field.

12. The method of claim 4, wherein the visually guiding object extends distally past the perimeter.

13. The method of claim 4, wherein the signals are generated in response to being exposed to an alternating magnetic field.

14. The method of claim 4, wherein the first axis of symmetry and the second axis of symmetry are perpendicular relative to each other.

15. The method of claim 4, wherein the two sensor coils are located proximally relative to the visually guiding object.

* * * * *